1

United States Patent
Taleyarkhan

(10) Patent No.: US 6,603,122 B2
(45) Date of Patent: Aug. 5, 2003

(54) PROBE FOR CONTAMINATION DETECTION IN RECYCLABLE MATERIALS

(75) Inventor: Rusi Taleyarkhan, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 09/864,693

(22) Filed: May 24, 2001

(65) Prior Publication Data

US 2002/0175288 A1 Nov. 28, 2002

(51) Int. Cl.⁷ .............................................. G01N 23/222
(52) U.S. Cl. ................. 250/358.1; 250/359.1; 250/360.1; 250/269.6; 250/370.05; 250/390.04; 250/390.05
(58) Field of Search .......................... 250/358.1, 359.1, 250/360.1, 269.6, 269.7, 269.8, 370, 390.04, 390.05; 75/10, 687; 266/901

(56) References Cited

U.S. PATENT DOCUMENTS

| | | | |
|---|---|---|---|
| 5,186,622 A | * | 2/1993 | Gillespie et al. ............... 432/13 |
| 5,539,788 A | * | 7/1996 | Ruddy et al. ................ 376/159 |
| 5,825,030 A | * | 10/1998 | Hurwitz et al. ........... 250/358.1 |
| 5,982,838 A | | 11/1999 | Vourvopoulos |
| 6,134,289 A | * | 10/2000 | Peurrung et al. ............ 376/153 |

* cited by examiner

Primary Examiner—Constantine Hannaher
Assistant Examiner—Timothy Moran
(74) Attorney, Agent, or Firm—Akerman Senterfitt

(57) ABSTRACT

A neutron detection system for detection of contaminants contained within a bulk material during recycling includes at least one neutron generator for neutron bombardment of the bulk material, and at least one gamma ray detector for detection of gamma rays emitted by contaminants within the bulk material. A structure for analyzing gamma ray data is communicably connected to the gamma ray detector, the structure for analyzing gamma ray data adapted. The identity and concentration of contaminants in a bulk material can also be determined. By scanning the neutron beam, discrete locations within the bulk material having contaminants can be identified. A method for recycling bulk material having unknown levels of contaminants includes the steps of providing at least one neutron generator, at least one gamma ray detector, and structure for analyzing gamma ray data, irradiating the bulk material with neutrons, and then determining the presence of at least one contaminant in the bulk material from gamma rays emitted from the bulk material.

39 Claims, 8 Drawing Sheets

Table 1. Atomic Densities (mol/cc) For Various Subtsances

| Material | Approximate Atomic Density (mol/cc) | | | |
|---|---|---|---|---|
| | Hydrogen | Carbon | Nitrogen | Oxygen |
| Dynamite | .048 | 0.015 | 0.015 | 0.06 |
| Cocaine | .065 | 0.05 | 0.001 | 0.018 |
| Sugar | 0.1 | 0.06 | | 0.05 |
| Alcohol | 0.1 | 0.03 | | 0.02 |
| Paper | 0.04 | 0.03 | | 0.025 |

*FIG. 1*

Table 3. Gamma Energy of Selected Elements of Interest to Aluminum Industry Situations

| Element | Gamma Energy (Mev) | Notes |
|---|---|---|
| Hydrogen | 2.223 | Thermal neutron capture; prompt |
| Carbon | 4.4 | (n,n'g); prompt-fast |
| Oxygen | 6.13 | Prompt-fast Inelastic scattering |
| Nitrogen | 10.83 | Prompt-thermal inelastic |
| Chlorine | 6.11, 2.23 | Prompt-thermal, inelastic |
| Aluminum | 8.43, 1.013, 1.719, 2.139<br>1.799, 4.133, 4.26, 4.734, 7.724 | Inelastic interactions-delayed<br>Capture interactions-thermal |
| Iron | 0.3522 | Thermal capture |
| Mercury | 0.3681 | |
| Cadmium | 0.5586 | |
| Silicon | 10.6 | Thermal capture |
| Lead (Pb-207m) | 1.063 | |

FIG. 2

PROBE FOR CONTAMINATION DETECTION IN RECYCLABLE MATERIALS

STATEMENT REGARDING FEDERALLY SPONSORED RESEARCH OR DEVELOPMENT

The United States Government has rights in this invention pursuant to Contract No. DE-AC05-00OR22725 between the United States Department of Energy and UT-Battelle, LLC.

FIELD OF THE INVENTION

This invention relates generally to an apparatus and method to detect the identity and concentration of substances in recyclable materials.

BACKGROUND

The detection of various substances such as water, butane from butane lighters, heavy metals and fertilizers in bulk volumes to be recycled, such as sows, has significant safety and economic significance. Sows are rectangular blocks of scrap aluminum weighing about 1,500-lb. each. Sows and scrap bales are commonly assembled in the aluminum recycling industry, sows being normally formed from a plurality of bales or refined metals. The presence of such substances even in relatively low concentrations can result in violent explosions when the bulk volumes to be recycled are loaded into melting furnaces during a typical recycling process. For example, if the water content exceeds a certain level or if significant levels of oxidizers are present, such as can be provided by butane from butane lighters and ammonium nitrate from fertilizers, catastrophic explosions can result.

Current empirically-derived practices for detecting such substances involve preheating sows for extended periods of time to evaporate an unknown quantities of water and other substances contained within the sow. For example, a typical preheating step can be performed for 6 hours at 700° F. This practice is time-consuming, energy intensive and dependent on closely following stringent operational guidelines derived from empirical experience. The amount of energy consumed for preheating aluminum sows alone is approximately equal to the amount of energy it takes to melt the aluminum sows. Furthermore, investments in and maintenance of preheat furnaces are required to support the moisture evaporation step used in conventional aluminum recycling processes.

Because the moisture level is not measured in conventional aluminum recycling, a preheating step is generally required to remove moisture, whether the moisture level entrapped in the so-called shrinkage cavities of sows is above or below a safe level. This results in the performance of a preheating step in instances when the preheating step may be unnecessary. Preheating practices followed are conservative and result in significant economic costs. Typical shrinkage cavities in 1,500-lb sows can accumulate volumes of water, from sources such as rainfall, in amounts typically from approximately 0.25 to 1.25 gallons (about 1 to 4 liters) per sow.

The existence of contaminating substances, such as lead, in scrap bales can also completely void the quality of the finished product. Accordingly, it is also important to detect and remove these substances, prior to bales being charged into furnaces. Current practice involves manually searching through selected bales to identify certain contaminating substances prior to charging furnaces.

X-rays are generally not useful as applied to contamination detection in bulk volumes, and accordingly are not used for this purpose. X-rays can be used to produce sharp images as well as density-dependant shading of interrogated objects. However, X-rays primarily provide information relating to the bulk properties of an object, and cannot provide substance-specific information. As a result, the application of an X-ray system to a sow to detect moisture cannot determine whether a density difference detected is due to an empty cavity, a cavity filled with water, some potentially explosive compound, or some other cause. Ultrasound techniques, which can be useful when used for crack or flaw detection, cannot be used for contaminant detection because ultrasound typically generates considerable scattering-induced noise and is also incapable of identifying specific substances.

Methods are used between the melt and casting steps to detect and remove hydrogen and unwanted inclusions, the inclusions being mainly oxides of elements such as magnesium and aluminum. The current practice typically used for detecting hydrogen involves use of the so-called Alscan probe, which is based on monitoring the thermal conductivity of a "sipped" sample drawn from a bulk material. For inclusion detection, a Limca probe is utilized which also uses small samples and detects inclusions via, monitoring electrical resistance changes from sipped samples. These techniques are both intrusive techniques which monitor small samples, require expensive equipment and cannot identify specific substances. Thus, current techniques do not provide the ability to assess bulk volumes of material, cannot detect contaminants with specificity, and cannot locate the position of contaminants within a given bulk volume.

A neutron detection system for detection of contaminants contained within a bulk material during recycling includes at least one neutron generator for neutron bombardment of a bulk material. At least one gamma ray detector is provided for detection of gamma rays emitted by contaminants within the bulk material responsive to the neutron bombardment. A structure for analyzing gamma ray data is communicably connected to the gamma ray detector, the structure for analyzing gamma ray data adapted to determine the presence of at least one contaminant in the bulk material.

The system can include a neutron reflector for reflecting at least a portion of neutrons which pass through the bulk material back into the bulk material, the neutron reflector disposed on an end of the bulk material distal to an end of the bulk material which receives an initially incident neutron beam emitted from the neutron generator. The neutron reflector can be made from Be, beryllium oxide and graphite. The system can include a structure for scanning a neutron beam emitted from the neutron generator across a portion of the bulk material to identify portions of the bulk material having contaminants. Discrete locations having contaminants can be identified with a 2-dimensional, or more preferably, with a 3-dimensional description.

The system can include a structure for removing detected contaminants from the bulk material. The structure for removing contaminants can be adapted to direct an energetic beam at discrete locations of the bulk material found to have contaminants. The structure for removing contaminants can be selected from a microwave source, an infrared and an acoustical source. Preferably, the structure for removing contaminants is an ultrasonic source, provided the contaminants are fluid contaminants.

The system can comprise at least two neutron generators, the neutron generators emitting at least two distinct neutron energy spectrums. The first neutron generator can emit neutrons having average energies of least 6 MeV and a second neutron generator can emit neutrons having average energies less than the first neutron generator. The first neutron generator can be a deuterium-tritium (D-T) generator and the second neutron generator can be a deuterium—deuterium (D—D) generator or an isotopic generator.

The bulk material for recycling can be scrap aluminum. The aluminum can be in the form of at least one sow. The structure for analyzing gamma ray data can be adapted to determine the identity, concentration and locations of contaminants in the bulk material.

A neutron detection system includes at least one neutron generator for neutron bombardment of a material, at least one gamma ray detector for detection of gamma rays emitted by the material responsive to the neutron bombardment, and a neutron reflector for reflecting at least a portion of the neutrons which pass through the material back into the material. The neutron reflector is disposed on an end of the material distal to an end of the material which receives an initially incident neutron beam emitted from the neutron generator. A structure for analyzing gamma ray data is communicably connected to the gamma ray detector, the structure for analyzing gamma ray data adapted to determine the presence of at least one substance in the material.

In another embodiment of the invention, a neutron detection system includes at least two neutron generators, the neutron generators emitting at least two distinct neutron energy spectrums for neutron bombardment of a material. At least one gamma ray detector is provided for detection of gamma rays emitted from the material responsive to the neutron bombardment, and a structure for analyzing gamma ray data communicably connected to the gamma ray detector, the structure for analyzing gamma ray data adapted to determine the presence of at least one substance in the material.

In another embodiment of the invention, a neutron detection system includes at least one neutron generator for neutron bombardment of a material, and at least one gamma ray detector for detection of gamma rays emitted by the material responsive to the neutron bombardment. A structure for analyzing gamma ray data is communicably connected to the gamma ray detector, the structure for analyzing gamma ray data adapted to determine the presence of at least one contaminant in the material. A structure for scanning a neutron beam emitted from the neutron generator across a portion of the material is provided to enable identifying portions of the material having contaminants. The system can include a structure for reducing the concentration of contaminants found in the locations having contaminants without substantially altering a composition of the material.

A method for recycling bulk material having unknown levels of contaminants includes the steps of providing at least one neutron generator for neutron bombardment of a bulk material and at least one gamma ray detector for detection of gamma rays emitted by contaminants within the bulk material responsive to the neutron bombardment. A structure for analyzing gamma ray data is communicably connected to the gamma ray detector, the structure for analyzing gamma ray data adapted to determine the presence of at least one contaminant in the bulk material. The bulk material is irradiated with emitted neutrons, and the presence of contaminants in the bulk material is determined from gamma rays emitted from the bulk material. The method can include the step of melting the bulk material without treatment to remove the contaminants, provided the determined concentration of contaminants are below predetermined limits.

The bulk material can be aluminum. In the case of bulk aluminum, the method can include the step of melting the bulk aluminum without treatment to remove the contaminants, such as water, provided the determined concentrations of the contaminants are below predetermined limits.

The method can include the step of reflecting at least a portion of the neutrons which pass through the bulk material back into the bulk material. The method can also include the step of scanning a neutron beam emitted by the neutron generator across a portion of the bulk material, the scanning identify portions of the bulk material having contaminants. The locations having contaminants can be represented in 2-dimensions, or more preferably, in 3-dimensions.

The method can include the step of determining at least one of the identity, concentration and location of contaminants in the bulk material. Contaminants can be removed by directing energy emitted from an acoustical source onto discrete locations of the bulk material found to have contaminants. Acoustical removal is particularly attractive when contaminants are fluids.

At least two neutron generators can be provided, the generators emitting at least two distinct neutron energy spectrums. The generators can include a first neutron generator emitting neutrons having energies of at least 6 MeV and a second neutron generator emitting neutrons having a lower average energy than the first neutron generator. The second generator can be a D—D generator or an isotopic generator. The method can include the step of moderating neutrons emitted by the second generator prior to irradiating the bulk material. The bulk material can be at least one sow.

In another embodiment of the invention, a method of moisture detection includes the steps of providing at least one neutron generator for neutron bombardment of a material, and at least one gamma ray detector for detection of gamma rays emitted by the material responsive to the neutron bombardment. A structure for analyzing gamma ray data is communicably connected to the gamma ray detector, the structure for analyzing gamma ray data adapted to determine the presence of water if present in the material. The material is irradiated with emitted neutrons. The presence and concentration of water in the material is determined from gamma rays emitted from the material. The method can include the step of identifying portions of the material having water. Preferably, the identifying step includes representing locations found having water in 2-dimensions, or more preferably, in 3-dimensions.

In yet another embodiment of the invention, a method for identifying discrete locations of contaminants within a bulk material includes the steps of providing at least one neutron generator for neutron bombardment of bulk material, and at least one gamma ray detector for detection of gamma rays emitted by contaminants within the bulk material. A structure for analyzing gamma ray data is communicably connected to the gamma ray detector is provided, the structure for analyzing gamma ray data adapted to determine the presence of at least one contaminant in the bulk material. A first portion of the bulk material is irradiated with emitted neutrons and the presence and concentration of contaminants in the first portion are determined from gamma rays emitted from the first portion. The neutron generator is moved to permit irradiation of another portion of the bulk material, the other portion different from the first portion. The other portion is irradiated with neutrons and the presence and concentration of contaminants in the other portion is determined from gamma rays emitted from the other portion.

The first portion can be substantially the entire bulk material, the other portion being a portion less than the entire bulk material. The method can include the step of scanning at least one of the neutron generators across a surface of the bulk material, where a plurality of portions of the bulk material can be tested.

DESCRIPTION OF THE DRAWINGS

A fuller understanding of the present invention and the features and benefits thereof will be accomplished upon review of the following detailed description together with the accompanying drawings, in which:

FIG. 1 is a table showing atomic densities of specific elements for selected substances.

FIG. 2 is a table showing gamma ray energies of selected elements of special interest to the aluminum recycling industry.

DETAILED DESCRIPTION OF THE INVENTION

Figure 3:
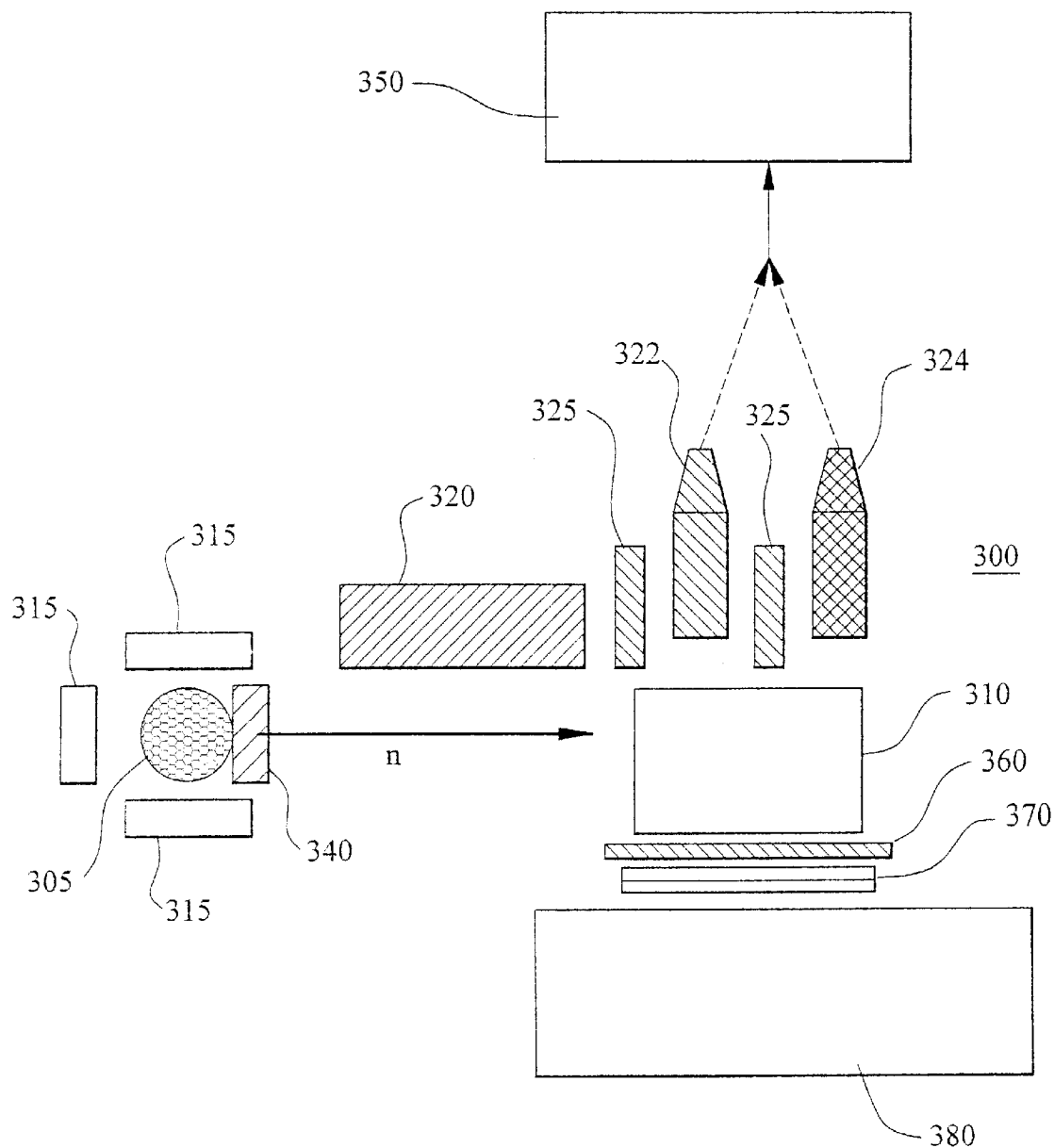
FIG. 3 illustrates a schematic of a neutron detection system having the neutron source and detector located separately, according to an embodiment of the invention.

A non-intrusive neutron based detection system and method can be used to determine the presence of contaminants in a given material. The identity of specific contaminants, the concentration of the detected contaminants, and the location of detected contaminants can be provided, the location information having spatial resolution capabilities to within a discrete portion within a given volume. The volume can be a bulk volume for recycling, such as an aluminum sow.

In one embodiment of the invention, a neutron based detection system can be used to detect specific contaminants within a bulk material during recycling. The system can provide significant energy savings and safety improvements over current practices, and can significantly enhance the cost competitiveness of various recycling processes, such as the aluminum recycling process commonly used in the aluminum industry. The invention can be used to examine large bulk volumes with specificity, and has no significant memory effects from previously-examined samples.

Neutron probes can be used to identify the existence of various types of compounds with specificity because compounds contain elements in unique quantities and ratios. The unique quantities and ratios of elements permits specific substances to be differentiated from one another through the emission of gamma rays from atomic nuclei bombarded by neutrons. For example, water, various hydrocarbons, and potentially explosive compounds such as fertilizers, contain elements such as H, C, N, O, P, S, Cl in quantities and ratios that permit specific substances containing these elements to be differentiated from on another through neutron bombardment and analysis of gamma rays emitted from nuclei of the bombarded elements.

FIG. 1 provides atomic densities for some common selected substances. As can be noted from FIG. 1, unique combinations of atomic densities are characteristic for compounds generally, such as each of the compounds listed in FIG. 1.

When an appropriate neutron beam is incident on a substance, nuclear reactions result which can give rise to unique signatures in the form of emitted gamma ray spectra and other such phenomena that can be correlated with the various elemental quantities present in the substance. Neutron interactions with nuclei of elements excite nuclei via reactions including elastic, inelastic and absorption reactions. Once excited, specific gamma rays are emitted as a result of (n,g), (n,n'), (n,p), and other interactions. For example, when neutrons of the proper energy range strike hydrogen atoms in water, gamma rays are emitted from hydrogen nuclei with an energy level of approximately 2.23 MeV. Detecting the presence of such an emission along with the amplitude of the emission signal can be interpreted by appropriate analysis equipment to provide a clear indication of the presence and quantity of the substance being interrogated.

Identification of specific substances can be provided by apparatus and software for analysis of gathered gamma ray data emitted by neutron radiated nuclei. Structures for analyzing gamma ray data are communicably connected to one or more gamma ray detectors, the structures for analyzing gamma ray data adapted to determine the presence of at least one contaminant in a neutron irradiated material. As used herein, the phrase "communicably connected" refers to the relationship where a first apparatus, such as a gamma ray detector, collects data and transmits at least a port ion of the data collected to a second apparatus, such as a gamma ray analyzer. Transmission can be performed by any appropriate communication method, including, but not limited to wired, wireless and optical communications.

For example, Perkin-Elmer Corporation, 100 Midland Road, Oak Ridge, Tenn. 37831 provides a DSpeC™ spectrometer for detecting emitted gamma rays and GammaVision™ analysis software, together capable of identifying specific substances from acquired gamma ray data emitted by neutron radiated nuclei.

The efficiency and cost of neutror generation and detection will vary with the type of neutron source (or sources) used, the type of detector(s) and analyzer used, and the shielding used. Typical technical specifications targeted specifically for aluminum industry recycling operations include detection of 0.5 volume % and higher moisture, 0.01 ml to 100 ml per 100 grams of Al for dissolved hydrogen to 100 ppm or higher in the melt, and 1 weight % or more of unwanted metals such as lead. Assay time is typically in the range of 1 to 5 minutes. Sows typically weigh approximately 1,500 pounds. Surrounding structures are generally concrete, metal such as steel or aluminum or wood platforms.

Contaminants can be concentrated at a single location, distributed randomly, or dispersed on a surface or within the bulk aluminum. Thus, the above specifications combined with surrounding conditions and contamination distribution in the bulk material if known, can be used as a basis for appropriate component choices and system set up parameters.

Neutron generators can generally be classified into two categories. Accelerator driven sources, such as deuterium-tritium (D-T) neutron generators, produce substantially mono-energetic neutrons having energies of either approximately 2.6 MeV or 14 MeV. Isotopic sources continuously produce neutrons from the decay of radioactive materials and accordingly result in a wide range of neutron energies. Thermal neutrons are neutrons having energies of a fraction of an electron volt (eV) to several electron volts, these neutrons having velocities comparable to the random motion of atoms in materials. The emission of gamma rays of interest for detecting appropriate elements in material volumes is dependent on the incident neutron energy and also on the specific type of resulting nuclear interactions.

Two basic forms of neutron sources can preferably be used with the invention depending on the system being configured for a given application. These preferred sources are either an isotopic source (such as Cf-252, Pu-Be) or neutron generators that use D-T reactions to produce 14 MeV neutron beams, the D-T sources capable of being configured as pulsed neutron generators (PNG) through appropriate use of a suitable moderator. Due to proliferation concerns, Pu-Be sources are not preferred. However, Cf-252 sources are commercially available and represent a lower-cost option. However, these sources can require considerable shielding when not in use since they produce neutrons continuously. The neutrons produced by Cf-252 sources have an emission spectrum that peaks around 2.5 MeV and then tapers off toward 6–7 -MeV to very low levels. These sources are not suitable for interrogating elements that require high activation energies, such as O and C, since the time required for counting a sufficient number of emitted gamma rays can get too large. However, when interrogation requires less than 2.5 MeV neutron energies, Cf-252 sources can be just as efficient and preferable, such as for interrogating H, Fe, N, Si.

Portable pulsed neutron generator tubes are available from a variety of vendors such as MF Physics, 5074 List Drive, Colorado Springs, Colo. 80919, or Activation Technology Corporation (ATC), 2816 Janitell Road Colorado Springs, Colo. 80906. These are generally portable sources which can be turned on and off remotely, but are typically expensive. These sources produce 2.5 MeV or 14 MeV neutrons and can accordingly generally be used across the spectrum of elements of interest. However, as these sources are used, they become increasingly depleted and need to be periodically refurbished. Therefore, the PNG may be useful to use judiciously in a hybrid form, such as side by side with an isotopic source.

For example, carbon and oxygen atoms are preferably detected with fast neutrons, fast neutrons being neutrons having energies greater than 6 MeV, and preferably in the 14 MeV range. On the other hand, other elements, such as hydrogen, are generally detected based on capture of thermalized neutrons. Available PNGs can produce "fast," or high-energy neutrons as well as thermal neutrons. For example, during pulses having a duration of about 10 microseconds fast neutrons can be emitted, while during gaps between fast neutron pulses some of the high energy neutrons can be passed through a neutron moderator, which slows high energy neutrons down, creating thermal neutrons.

The process of producing gamma ray photons by the interaction of nuclei of the inspected material with neutrons from a neutron generator can be effected by either of three processes. These include fast neutron, thermal neutron and neutron activation reactions. Thermal neutron reactions occur by the capture of a neutron by a nuclei producing an isotope which is de-excited by the emission of gamma radiation. Fast neutron reactions result in the inelastic scattering of a neutron on a nucleus which is de-excited by the emission of prompt gamma radiation. This interaction occurs only with fast neutrons having a sufficient energy being at least equal to that of the prompt gamma radiation. Finally, neutron activation reactions occur by the activation of a nuclei by a thermal or fast neutron which, creates a radioactive nuclei having a certain life and which disintegrates by emitting activation gamma radiation.

A variety of atoms can be detected from neutron activated material. For the aluminum recycling industry, a preferred neutron probe should be capable of detecting substantially all the elements cited in the table provided in FIG. 2. FIG. 2 also indicates the type of interaction which is most prominent under the heading entitles "Notes." The gamma rays of interest are typically given off by prompt reactions due to fast neutron interactions, and are given off in the time span of typically less than 10 $\mu$s. Gamma rays given off due to prompt interactions from capture of thermal neutrons are given off after about 20 $\mu$s and can be collected over 80 to 100 $\mu$s. Delayed emission of gamma rays due to activation of the elements such as Si, Na, P, Al are generally collected over several minutes. The time delay differences between elements is an important consideration when designing a system for gamma spectra collection in conjunction with a pulsed neutron generator.

It is noted from the above that, if a given application only requires hydrogen detection, a given neutron source which maximizes production of thermal neutrons will be preferred. Thermal neutron interactions with hydrogen will result in emission of 2.223 MeV gamma rays.

Applied to situations where both aluminum and hydrogen are present, such as aluminum recycling, the detector should preferably have sufficient resolution, being generally less than 1% to enable detection of the 2.223 MeV H Line in the presence of the 2.21 MeV Al gamma line. For sows and bales where moisture is the only item for detection, and no hydrides are present, a simple portable Cf or Pu-Be type isotopic source could be used to provide rapid-turnaround detection of hydrogen bound to one or more other atoms, if shielding requirements do not become onerous.

A similar situation exists for detection of nitrogen in the presence of silicon. Silicon is a ubiquitous material in the earth and in concrete, both of which give off gamma rays in the 10.6 and 10.83 MeV range following neutron bombardment of 14 MeV neutrons. For other elements which depend on gamma spectra in the higher range, such as C or O, faster emission would require the use of higher energy neutrons. Accordingly, tradeoffs are generally necessary.

Another design requirement of concern is the type of neutrons needed. A PNG producing about $2.0 \times 10^8$ n/s can be used with moderators to produce about $1.0 \times 10^7$ n/s of thermalized neutrons, making them ideal for detecting elements such as H and Fe. Fast neutrons from Cf-252 are much easier to thermalize. A Cf-252 $2.0 \times 10^7$ n/s source with moderators will produce $1.0 \times 10^7$ n/s of thermalized neutrons. Therefore, for thermal neutron-based detection, a PNG producing $2.0 \times 10^8$ n/s is equivalent to a Cf-252 source producing $2.0 \times 10^7$ n/s.

The shielding preferably used with the invention should follow the requirements as set by the United States Nuclear Regulatory Commission (USNRC) for allowable personnel dose as described in 10 C.F.R. Part 20. This regulation requires that the flux and dose from fast neutrons be maintained to less than 10 n/cm²-s and 100 mRem/week for a 40 hour week, respectively. Under the limits set by this regulation, a neutron source producing $1.0 \times 10^6$ n/s will require no shielding for personnel if the distance maintained from the source is greater than approximately 3 feet where the flux is estimated without shielding to be about 8.5 n/cm²-sec.

Thermal neutron production lead/tungsten shielding or borated paraffin/polyethelene may be used as shielding materials. Heavy elements, such as lead, could also be useful to shield from emitted gamma rays. Shielding of the source and detector system could also be used to appropriately collimate fast neutron beams when desired.

Also, when concrete is used as a shielding material, about 15 inches of concrete will reduce the dose by a factor of 10. This attenuation is likely conservative when applied to borated polyethylene of borated paraffin. Therefore, if a more powerful source of neutrons is to be used (e.g. $1.0 \times 10^7$ n/s), to keep dose levels at 1 ft below the acceptable levels, one would need to introduce about 1 ft of concrete shielding around the source. Alternately, the distance from the source can be designed or implemented to be more than 9 ft rather than 3 ft since the neutron flux is proportional to the square of the distance from a neutron source.

In general, the larger the neutron production rate, the larger the number of gamma rays that are generated by a bombarded material which can be counted. Larger neutron production rates accordingly provide faster detection. From a practical view for the aluminum industry where timing for detection is important, it is recommended that PNG and isotope sources be used with neutron generation rates in the $1.0 \times 10^8$ n/s range with appropriate shielding and/or sufficient distance maintained from the neutron sources when they are in operation.

Another important system component is the detector. Detector efficiency and resolution along with suitable cooling and counting systems are important detector features. As mentioned earlier, the detection of moisture through detection of hydrogen (H) in the presence of aluminum (Al), or for detecting nitrogen (N) in the presence of silicon (Si) will generally require detectors having the ability to resolve adjacent peaks in the detected spectra located within an energy range of 1% between respective peaks. In addition, good detection speed is generally required if used to meet Al-industry specifications. In these cases a high-purity germanium detector (HPGe) can preferably be used. For isotopes containing elements such as N, C and O, a 10% resolution will be adequate for obtaining appropriate counting statistics for which a Bismuth Germate (BGO) detector will be adequate for use, assuming absence of interference from other elements such as Si that may be present. A 100%+efficiency HPGe detector can be used to enable faster counting. HPGe detectors require cryogenic cooling and are generally operated in the 80–100° K. range using stream-lined cryostats with an internal heater to allow in-cryostat neutron damage repair and avoid lengthy shutdowns for annealing.

Ultimately, the detector system could preferably be connected to a standard multi-channel analyzer (MCA) system where counting and sorting of emitted photons can take place. Faster counting can be aided by using off-the-shelf transistor reset pre-amplifiers to achieve at least 1 Gev/s energy rates along with a high rate gated amplifier and a high (120%) efficiency detector with a collimator to get high signal to noise ratios.

FIG. 3 presents a neutron detection system 300, according to an embodiment of the invention. As shown, a neutron source 305, which may be a pulsed and/or isotopic source is placed on one side of the target 310. Shielding 315 is positioned around the source 305, the shielding being materials such as W or Pb shielding 315 provides an increase in thermal neutron production in addition to collimating the direct neutron flux in the forward direction with fast neutrons. A borated polyethylene or paraffin or graphite-type shield 320 is shown placed between the source 305 and the BGO and HPGe detectors 322 and 324, respectively, to minimize fast neutron damage to the normally sensitive detector elements 322 and 324. Detectors 322 and 324 are connected to multichannel analyzer (MCA)/data analyzer 350 which interprets gamma rays emitted from target 310. When neutron economy is an important factor, it is particularly useful to include neutron reflector 360, placed at the far end of the target 310 so as to reflect back as many neutrons as possible to the target 310.

Reflector 360 can be formed from materials which substantially reflect incident neutrons. For example, Be, beryllium oxide and graphite reflect neutrons via reduced absorption and provide good scattering. Some neutron capture also generally take places. For example, the total neutron absorption cross-sections (cm$^{-1}$) for water, Be, BeO and Graphite are 0.022, 0.0012, 0.00073, and 0.00032, respectively. The total neutron scattering cross-sections (cm$^{-1}$) for water, Be, BeO and Graphite are 3.4, 0.9, 0.5 and 0.4, respectively.

Figure 5:
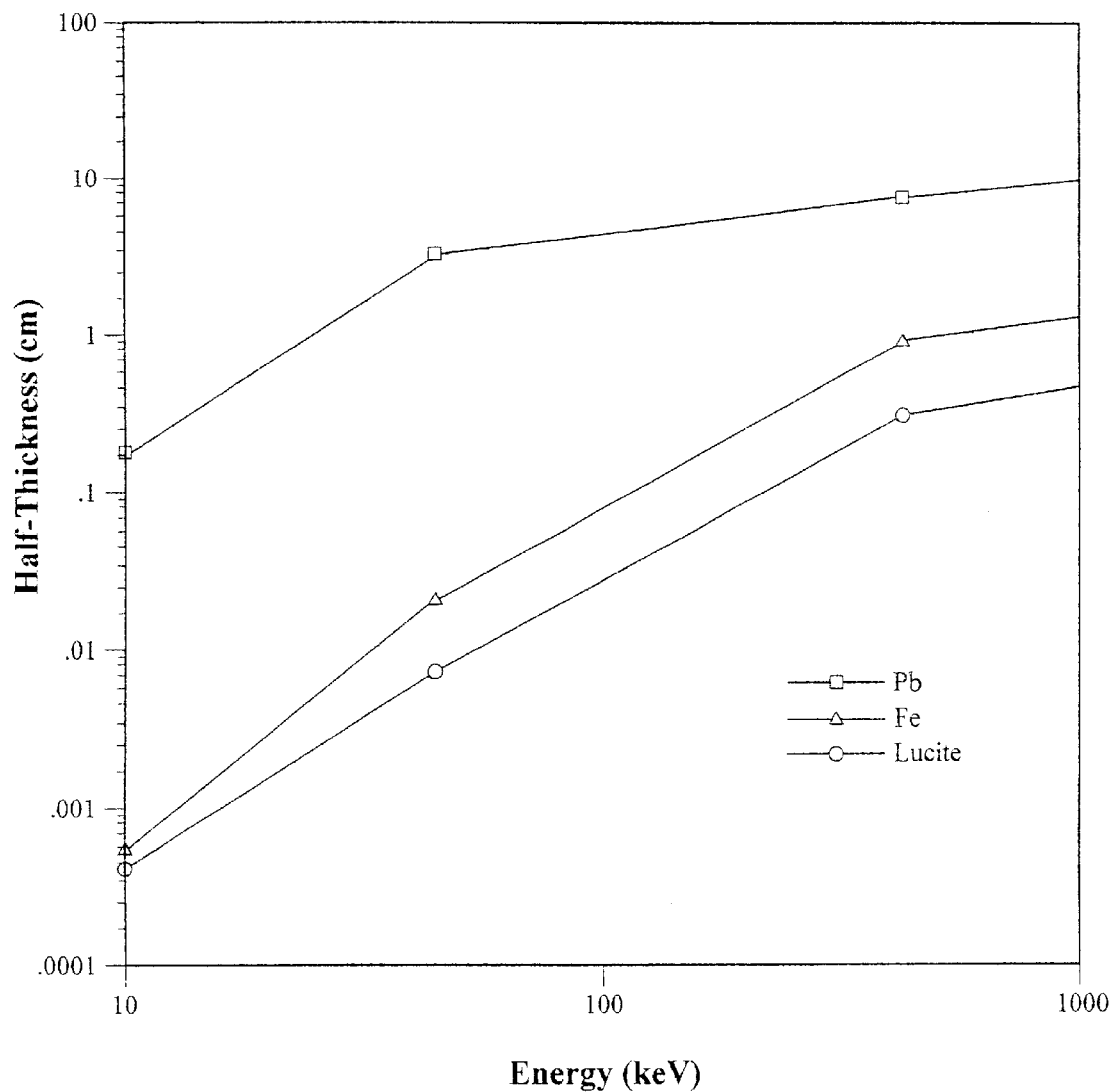
FIG. 5 illustrates the variation in half-thickness with energy for selected materials.

A gamma shield 370 can also be added to reduce gamma ray radiation from the substrate 380, substrate 380 commonly being a concrete floor. Gamma shield 370 is preferably placed between the neutron reflector 360 and the substrate 380 as shown in FIG. 3. The thickness of substrate 380 will depend on the type of shield chosen (ranging from lead to plastics) and the gamma energy levels involved. The shielding thickness should ideally be chosen to reduce the background gamma energies by about 90%. The curves provided in FIG. 5 can be used to estimate the shielding thickness required to achieve a desired reduction in gamma ray energies. For example, to reduce a 1 MeV gamma ray by 90% in intensity using lead shielding would require a thickness of 2 cm (about 0.8 inches). However, to avoid cosmic ray interactions this thickness should preferably be kept below approximately 4 to 5 inches.

For applications which monitor elements such as H and N, which are generally activated with thermal neutrons, a moderator 340 being preferably removable, can be placed between the source 305 and the target 310 to maximize thermal neutron production. For other situations, such as when elements to be detected are preferably activated by fast neutrons, such as C and O, moderator 340 will generally not be included in the system.

When both fast and thermal neutrons are needed, a fast neutron source can be adapted for pulsed operation, such as thermal neutron production between pulses when the fast neutrons are thermalized. Thus, moderator 340 can be operable during a first interval of time to produce thermal neutrons and excluded during the other interval of time to produce fast neutrons. An alternative is the use of two or more neutron sources 305 which can operate simultaneously, with at least one source producing fast neutrons (having no moderator) and at least one source producing thermal neutrons, generally obtained through use of moderator 340.

Heavy element (e.g., tungsten) shielding 325 can preferably be placed around the detectors 322 and 324 to act as collimators. Thin lead shielding or LiF is preferably used at the reading face of detectors 322 and 324 to prevent damage from thermal neutrons. Detectors, preferably having a size of about 3 inches in diameter, can be placed at a set distance from the target 310. The targets 310 are typically, but not necessarily, sows, bales and melt streams.

Two detectors are preferably supplied to system 300. A low-cost BGO detector 322 can be used for situations wherein high resolution is not required. A high resolution and high efficiency detector is generally required, especially for detecting compounds having N type elements that give off gamma rays in the 10 MeV range where efficiency is usually poorer for detectors such as NaI and BGO. For relatively slow counting, a BGO 322 detector could be used, whereas, for fast counting a higher-cost HPGe detector 324 may be used.

Figure 4:
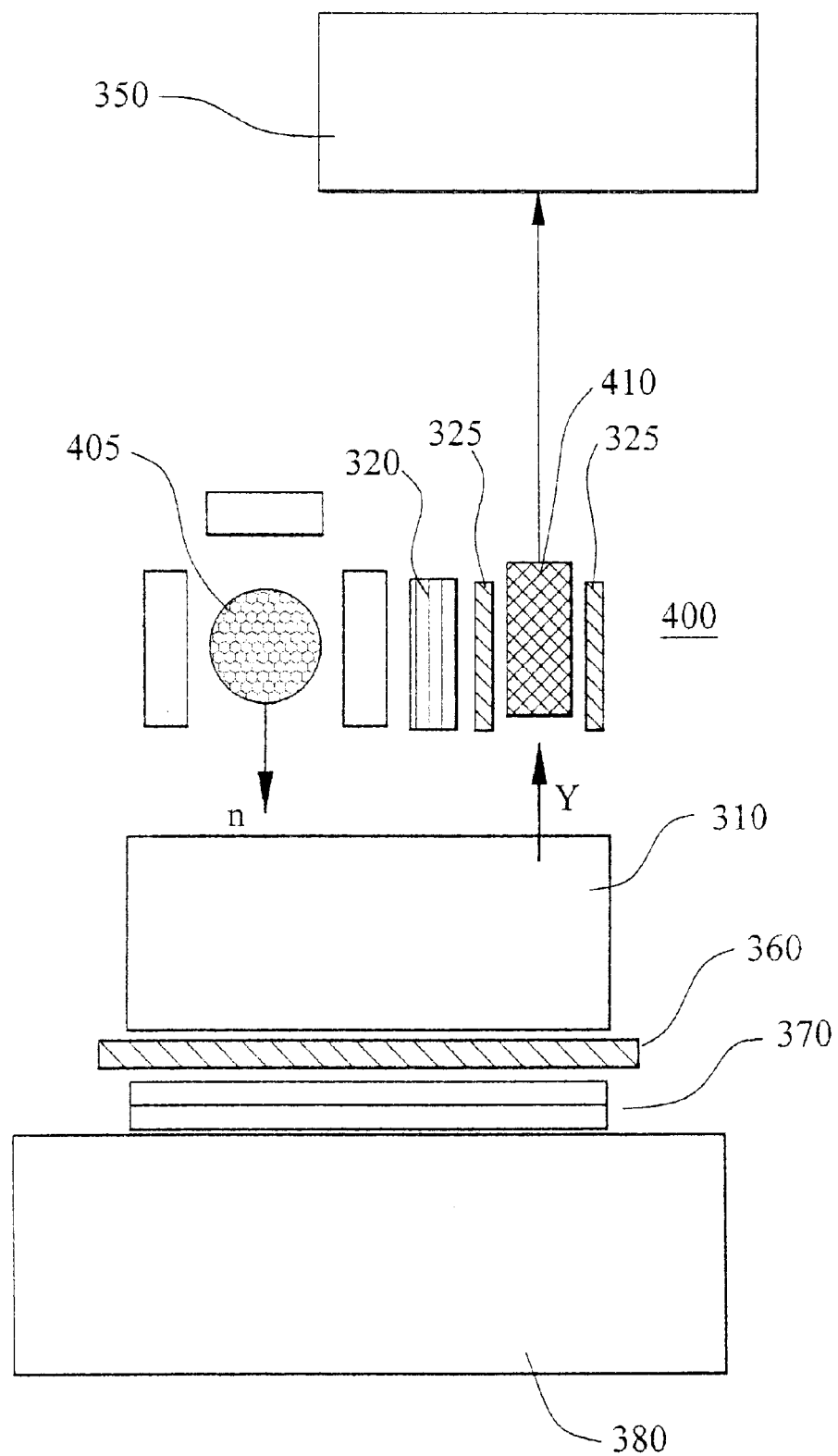
FIG. 4 illustrates a schematic of a neutron detection system having the neutron source and detector located adjacent to one another, according to another embodiment of the invention.

An alternate neutron detection system 400 is shown in FIG. 4. In this embodiment, the source 405 and detector 410 are located side-by-side, as opposed to remotely located as shown in FIG. 3. This configuration is particularly well adapted for situations in which a portable system is needed and one in which the source 405 and detector 410 are capable of being moved together.

The system configurations discussed can be used to assess the identity, concentration and location of contaminants. Before testing samples, it is preferable to calibrate the system to quantify and store background readings for the given combination of geometry and operation conditions of the source-detector 405/410 combination. Tests with targets 310 in place can then be made, where data derived can be adjusted for background gamma ray calibration data.

Now referring to FIGS. 6–9, once the source-detector system is calibrated, a two-staged assessment is preferably performed. In the first stage, a bulk assessment is performed where substantially the entire target material 310 is tested at a given time. During the bulk assessment, an evaluation is preferably made as to whether and to what extent a given recyclable material target 310, such as a metal target, contains contaminant elements and compounds of interest. For bulk assessment in the case of a side-by-side source and detector combination such as the source and detector shown in FIG. 4, the distance of the source-detector 610 from the target 310 is set to enable an appropriate solid angle subtended from the source-detector 610 such that substantially the entire target area is in receipt of neutron bombardment, and the resultant gamma rays can also reach the detector 610. If one or more contaminants, such as moisture is detected and determined to be above a certain predetermined level, the load may be either rejected, sorted by hand, or preferably further examined to more specifically locate and substantially remove the contaminants.

Figure 6A:
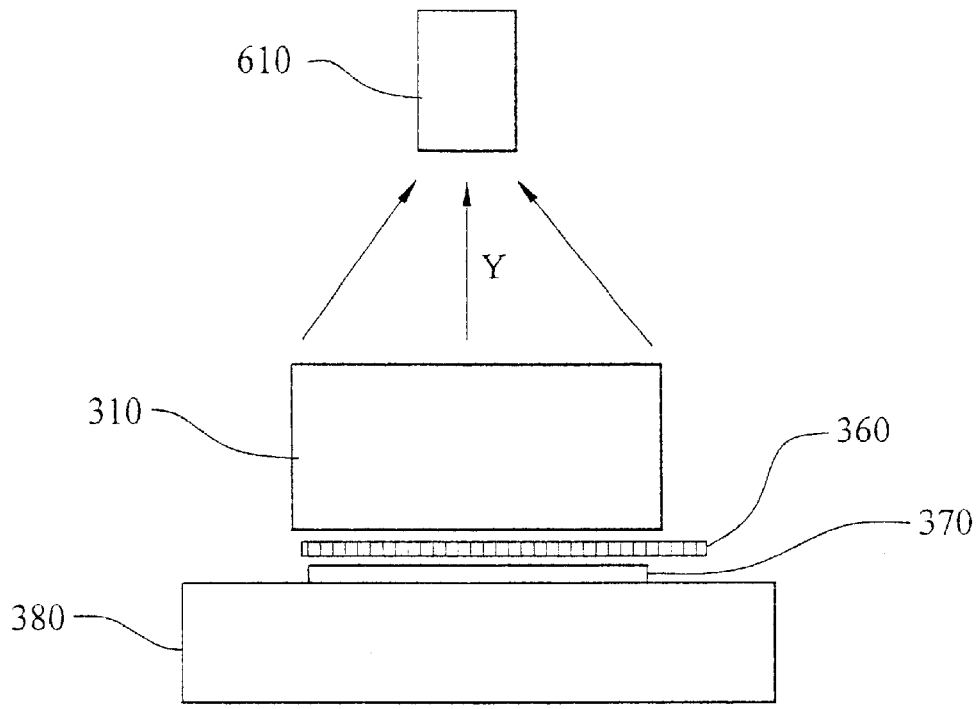
FIG. 6(a) illustrates a schematic of a neutron detection system adapted for assaying a bulk material, according to an embodiment of the invention.
Figure 6B:
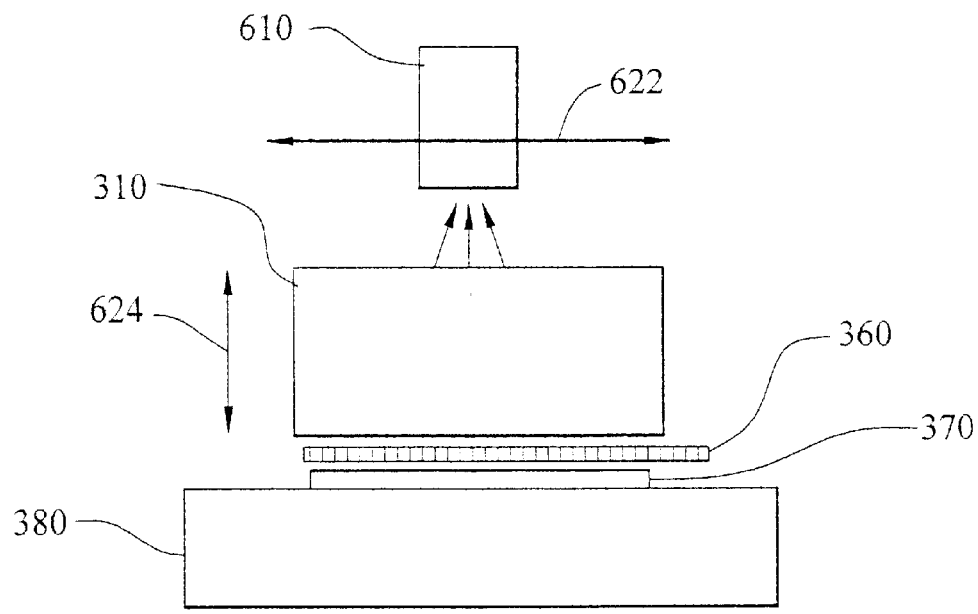
FIG. 6(b) illustrates a schematic of a neutron detection system adapted for assaying localized portions of a bulk material, the detector traversing the surface of the bulk material, according to another embodiment of the invention.

In a second stage, as shown in FIG. 6(*b*), a localized assessment can preferably be performed to search for the location of contaminants in the sows or bales generally comprising target 310. In this case, it is preferable to either collimate the neutron source 610 to transmit neutrons to a discrete portion of the target 310. This can be accomplished by bringing the collimated neutron source closer to the proper distance for a desired solid angle, or via movement of the detector(s). The source/detector 610 could also be configured as shown in FIG. 6(*b*) to include collimating lines to enable gamma ray detection from discrete portions of target 310.

The source/detector 610 can be translated to permit scanning which can be conducted in two or three dimensions to the degree of accuracy needed. Finer resolution can be achieved by decreasing the distance between the target and the neutron source or reducing the distance between collimators (not shown). Three dimensional coverage can be realized by scanning the source/detector 610 along two orthogonal planes, such planes 622 and 624. For example, plane 622 can be the x-y plane such as the top of the target 310, while plane 624 can be the x-z plane or the y-z plane, which can be sides of target 310.

A variety of translation systems can be used with the invention. For example, a gear driven system can provide the translation. The translation system moves either target 310 or source/detector 610 to provide relative movement between the same relative to source/detector 610. Higher levels of accuracy or reduced counting time would determine the level of neutron source strength. The higher the production, less the time for detection, the rate of scanning, and the type of detector used.

The system can include a structure for removing contaminants (not shown) which can operate automatically following the detection of contaminants. Once a contaminant such as moisture is detected having a concentration above a predetermined limit, a focused beam of energy can be directed towards the contamination for a period sufficient to dissipate the contaminant to at least a level below the predetermined concentration limit. Preferably, detection and dissipation can proceed simultaneously to improve system efficiency by limiting the dissipation time to the minimum period necessary to reduce the contaminant concentration to a set level.

If it is desired to remove moisture, a microwave or acoustical energy source may be used. However, if the target material is aluminum, an acoustical source will be preferred due to the significant absorption of microwaves by aluminum. The acoustical source can preferably be an ultrasonic source.

Structures for removing contaminants are selected so that the composition of the bulk material, such as aluminum, is not substantially altered. Thus, the neutron source energy and other operation settings selected to remove contaminants should not significantly melt, vaporize, oxidize or otherwise alter the composition of the bulk material.

Applied to aluminum recycling, following the detection of water above a predetermined concentration, an acoustical beam can be, directed toward the discrete moisture containing locations to evaporate the moisture. For example, water can be forced to cavitate and aerosolize using relatively low pressure fluctuations being only a few psi. As in a humidifier, the rate of removal is dependent on the energy of the acoustical source.

In another embodiment of the invention, the system can include at least two neutron generators, the neutron generators emitting at least two distinct neutron energy spectrums. For example, the first neutron generator can emit neutrons having energies around 14 MeV and a second neutron generator can emit neutrons having lower energies, such as energies around 2.5 MeV or an isotopic source (e.g. Cf-252) with a broad energy distribution having a peak at several MeV, for example, a CF-252 source has a peak at approximately 3 MeV. The second neutron generator preferably includes a moderator to produce thermal neutrons, provided substances to be detected to have elements such as H. Use of a Cf-252 isotopic source provides system economy compared to other neutron sources. However, Cf-252 sources need shielding since they are continuously producing radiation.

The first generator is preferably a D-T generator while the second generator can be a D—D generator. It is noted that D—D sources are approximately 10 times more efficient in generation of thermal neutrons as compared to D-T generators. Moreover, D—D sources are known to deplete at a faster rate as compared to D-T sources.

Figure 7:
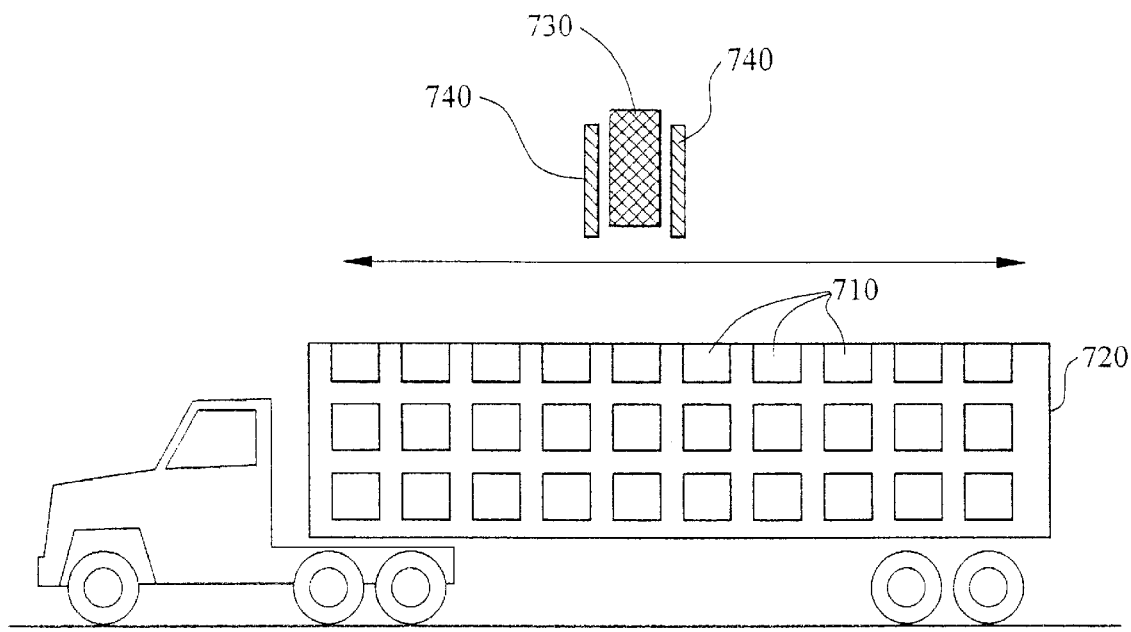
FIG. 7 illustrates a schematic of a neutron detection system adapted for assaying the breadth of a bulk volume of recyclable material, the recyclable material shown positioned in a vehicle, according to another embodiment of the invention.
Figure 8:
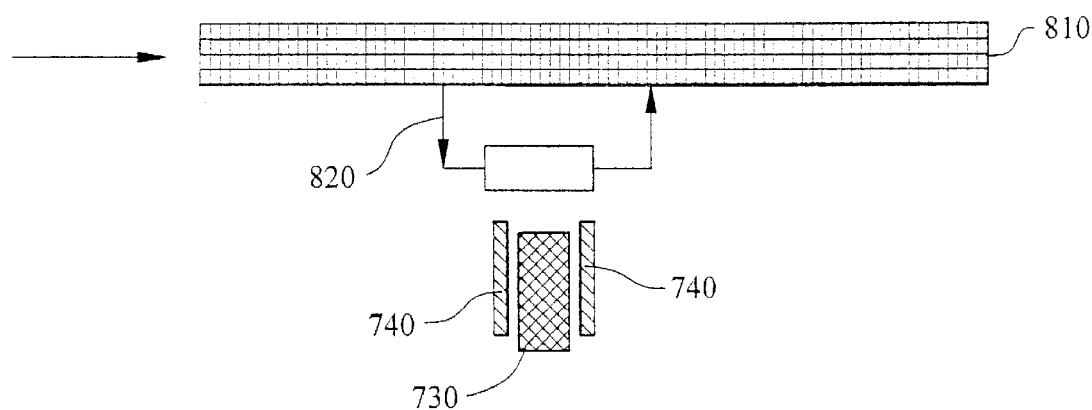
FIG. 8 illustrates a schematic of a neutron detection system adapted for assaying molten recyclable material flowing in troughs, according to another embodiment of the invention.

Various system exemplary configurations are shown in FIGS. 7 through 8 which can be used to assess bulk volumes such as sows, containers, trucks carrying sows and troughs carrying molten metal. For a bulk volume comprising stack of sows, the scanning geometry and detection arrangement could essentially be as depicted in FIGS. 3, 4 and 6. For detecting contaminants within bales/scrap 710 located on a truck 720, the solid angle chosen based on the distance between probe 730 and bales 710 may be set such that all bales 710 are simultaneously radiated. Alternatively, a one-pass scan can be used to analyze all bales 710 where probe 730, comprising at least one source and detector, is translated while covering the breadth (width) of bales 710 during a substantially linear translation to determine if contaminants above predetermined levels are present anywhere within the bale 710. If contaminants are detected, the load may be rejected, or else subjected to localized scanning for determining the actual locations of contaminants to permit removal. Removal is preferably performed by directing a focused beam of energy at the locations having the contaminants to dissipate the contaminants. The shielding 740 and resulting collimation around the source 730 can preferably be set to achieve minimal radiation risks to individuals positioned near the detection operation, such as truck drivers and inspectors.

When analyzing metals flowing in troughs 810, background radiation levels can become excessive. In this case, as shown in FIG. 8, a portion of the trough 810 is built with a metal, such as stainless steel, or a bypass 820 is put in place such that metal can be assessed separately by probe 730, positioned away from the trough 810 either after the melt has frozen or while the melt is still molten. For such configurations, the neutron based system may be supplemented with a particle/contaminant sizing system (not shown), such as a series of filters with various size openings to detect the size of particles in the flow stream. For situations wherein high temperature environments are prevalent, care should be taken to ensure that the detector system does not overheat, and which can cause degradation in detector performance and damage to the detector.

System configurations should preferably include a connection to an indicator system to provide warning when the neutron generator is operational and standard safety interlocks to terminate operation upon intrusion. Safety shielding should be placed using structural material such as concrete to meet 10 C.F.R. 20 requirements and other materials, such as graphite, lead, paraffin. The shielding should be placed depending on dimensions of the casthouse itself, to allow free access and mobility to personnel and still enable safe operation.

Figure 9:
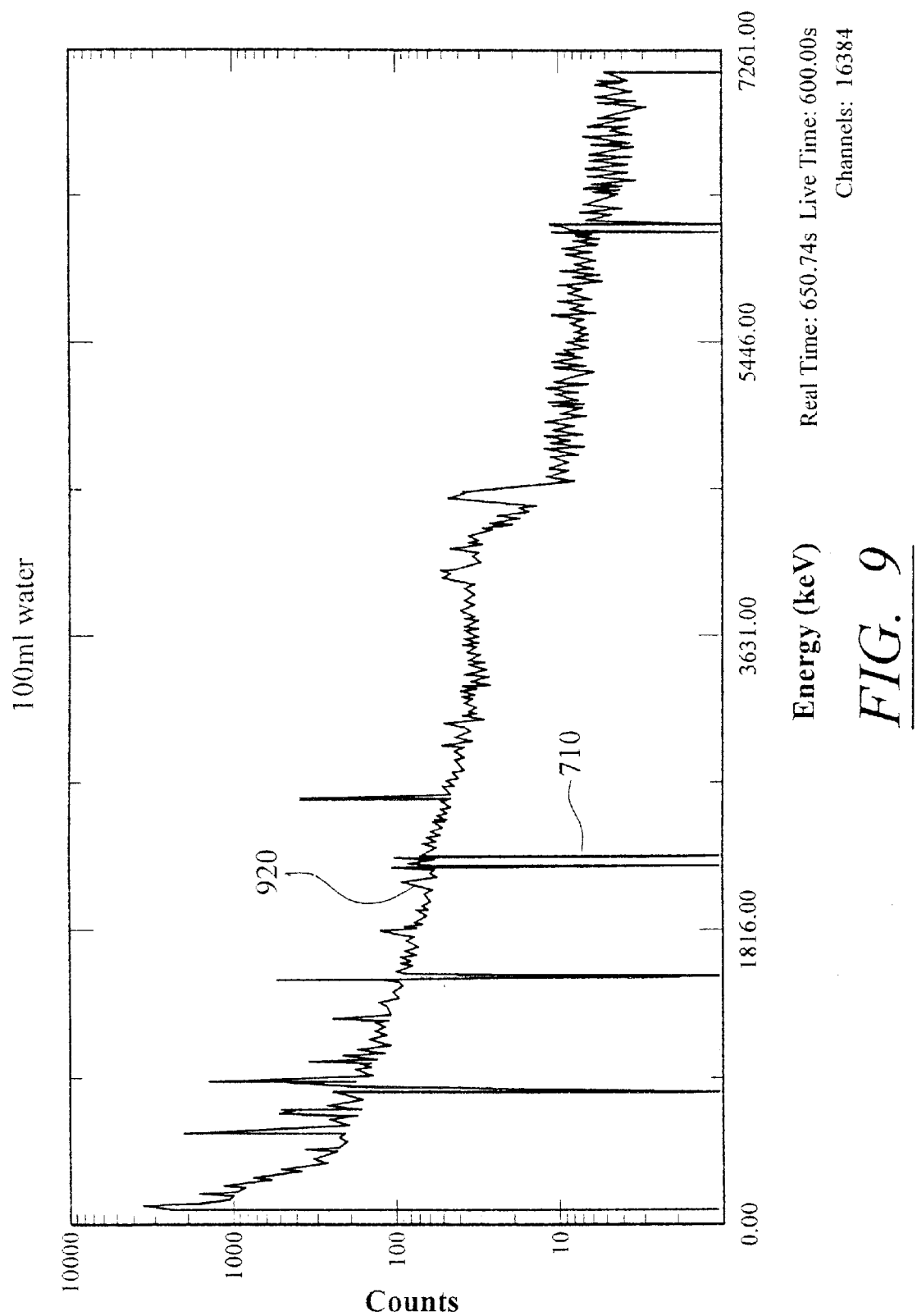
FIG. 9 illustrates a plot of collected gamma rays emitted from a sample, the sample including water.

EXAMPLE:

FIG. 9 shows a gamma ray spectra without adjustment for background gamma ray calibration data. The gamma spectra shown was derived from experiments performed over a 10 minute period with a Pu-Be source producing $1.0 \times 10^6$ n/s neutrons, a DSpec™ spectrometer coupled with GammaVision™ (software for analysis for Ge detector gamma ray spectra) from Perkin-Elmer. The experiment was conducted to test the operation of a neutron system for detection of hydrogen in water, the water located in an aluminum container having a liter of aluminum. It was found that the time it takes to detect the presence of 100 ml of water contained in a 1 liter aluminum vessel via the detection of hydrogen is approximately 10 minutes.

The experiment was performed without the thermalization of neutrons. Since gamma ray counts are directly proportional to the neutron flux, a 10 times larger neutron flux, could reduce the approximate detection time to the 1 minute range. Pre-thermalization of the neutron flux could also reduce the time further, but-may not be necessary since the technical specifications for the aluminum industry were met without requiring neutron thermalization. A hydrogen peak 910 detected at approximately 2.22 MeV is demonstrated in FIG. 9. The peak identified with reference 920 is an Al peak at approximately 2.21 MeV, demonstrating the system ability to resolve the 2.22 MeV H line from the 2.21 MeV Al line, the resolution of these respective peaks important regarding moisture detection for the aluminum recycling industry.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

I claim:

1. A neutron detection system for detection of contaminants during recycling, comprising:
   at least one neutron generator for neutron bombardment of a bulk material during recycling;
   at least one gamma ray detector for detection of gamma rays emitted by contaminants within said bulk material responsive to said neutron bombardment, and
   structure for analyzing gamma ray data communicably connected to said gamma ray detector, said structure for analyzing gamma ray data adapted to determine the presence of at least one contaminant in said bulk material.

2. The system of claim 1, further comprising a neutron reflector for reflecting at least a portion of neutrons which pass through said bulk material back into said bulk material, said neutron reflector disposed on an end of said bulk material distal to an end of said bulk material which receives an initially incident neutron beam emitted from said neutron generator.

3. The system of claim 2, wherein said neutron reflector is made from at least one reflective material, said reflective material being at least one selected from the group consisting of Be, beryllium oxide and graphite.

4. The system of claim 1, further comprising structure for scanning a neutron beam emitted from said neutron generator across a portion of said bulk material to identify portions of said bulk material having said contaminants, said scanning having components in at least two orthogonal planes.

5. The system of claim 4, wherein said structure for scanning identifies discrete locations of said contaminants using a 2-dimensional description.

6. The system of claim 4, wherein said structure for scanning identifies discrete locations of said contaminants using a 3-dimensional description.

7. The system of claim 1, wherein said at least one neutron generator comprises at least two of said neutron generators, said neutron generators emitting at least two distinct neutron energy spectrums.

8. The system of claim 7, wherein said neutron generators include a first neutron generator emitting neutrons having averages energies of least 6 MeV and a second neutron generator emitting neutrons having average energies less than said first neutron generator.

9. The system of claim 7, wherein said first neutron generator is a D-T generator and said second neutron generator is at least one selected from the group consisting of a D—D generator and an isotopic generator.

10. The system of claim 1, wherein said bulk material for recycling is aluminum.

11. The system of claim 10, wherein said bulk material is in the form of at least one sow.

12. The system of claim 1, wherein said structure for analyzing gamma ray data is adapted to also determine at least one selected from the group consisting of identity, concentration and location of said contaminants in said bulk material.

13. A neutron detection system for detection of contaminants contained within a bulk material, comprising:
   at least one neutron generator for neutron bombardment of said bulk material;
   at least one gamma ray detector for detection of gamma rays emitted by contaminants within said bulk material responsive to said neutron bombardment,
   structure for analyzing gamma ray data communicably connected to said gamma ray detector, said structure for analyzing gamma ray data adapted to determine the presence of at least one contaminant in said bulk material, and
   structure for removing detected contaminants from said bulk material.

14. The system of claim 13, wherein said structure for removing contaminants is adapted to direct an energetic beam at discrete locations of said bulk material found to have said contaminants.

15. The system of claim 14, wherein said structure for removing contaminants is at least one selected from the group consisting of a microwave source, infrared and an acoustical source.

16. The system of claim 14, wherein said structure for removing contaminants is an ultrasonic source.

17. A neutron detection system, comprising:
   at least one neutron generator for neutron bombardment of a material;
   at least one gamma ray detector for detection of gamma rays emitted by said material responsive to said neutron bombardment;
   a neutron reflector for reflecting at least a portion of neutrons which pass through said material back into said material, said neutron reflector disposed on an end of said material distal to an end of said material which receives an initially incident neutron beam emitted from said neutron generator;
   structure for analyzing gamma ray data communicably connected to said gamma ray detector, said structure for analyzing gamma ray data adapted to determine the presence of at least one substance in said material, and
   structure for scanning a neutron beam emitted from said neutron generator across said material to identify discrete portions in said material having said substance, said scanning having components in at least two orthogonal planes.

18. A neutron detection system, comprising:
   at least one neutron generator for neutron bombardment of a bulk material during recycling;
   at least one gamma ray detector for detection of gamma rays emitted by said bulk material responsive to said neutron bombardment;
   structure for analyzing gamma ray data communicably connected to said gamma ray detector, said structure for analyzing gamma ray data adapted to determine the presence of at least one contaminant in said bulk material, and
   structure for scanning a neutron beam emitted from said neutron generator across a portion of said bulk material to identify portions of said bulk material having contaminants.

19. The detection system of claim 18 further comprising structure for reducing a concentration of said contaminants found in said portions having contaminants without substantially altering a composition of said bulk material.

20. A method for recycling bulk materials having unknown levels of contaminants, comprising the steps of:
   providing at least one neutron generator for neutron bombardment of a bulk material and at least one gamma ray detector for detection of gamma rays emitted by contaminants within said bulk material responsive to said neutron bombardment, and structure for analyzing gamma ray data communicably connected to said gamma ray detector, said structure for analyzing gamma ray data adapted to determine the presence of at least one contaminant in said bulk material;
   irradiating said bulk material with said emitted neutrons, and
   determining the presence of said contaminants in said bulk material from gamma rays emitted from said bulk material.

21. The method of claim 20, further comprising the step of melting said bulk material without treatment to remove said contaminants, provided said determined concentration of said contaminants are below predetermined limits.

22. The method of claim 20, wherein said bulk material is aluminum.

23. The method of claim 22, further comprising the step of melting said bulk aluminum without treatment to remove said contaminants, provided said determined concentrations of said contaminants are below predetermined limits.

24. The method of claim 20, further comprising the step of reflecting at least a portion of neutrons which pass through said bulk material back into said bulk material.

25. The method of claim 20, further comprising the step of scanning a neutron beam emitted from said neutron generator across a portion of said bulk material, said scanning to identify portions of said bulk material having said contaminants.

26. The method of claim 25, further comprising the step of identifying discrete locations having said contaminants, said discrete locations represented in 2-dimensions.

27. The method of claim 25, further comprising the step of identifying discrete locations having said contaminants, said discrete locations represented in 3-dimensions.

28. The method of claim 20, further comprising the step of determining at least at least one selected from the group consisting of identity, concentration and location of said contaminants in said bulk material.

29. The method of claim 20, further comprising the step of removing said contaminants by directing energy emitted from an acoustical source onto discrete locations of said bulk material found to have said contaminants.

30. The method of claim 20, wherein said at least one neutron generator comprises at least two of said generators, said generators emitting at least two distinct neutron energy spectrums.

31. The method of claim 30, wherein said generators include a first neutron generator emitting neutrons having energies of at least 6 MeV and a second neutron generator emitting neutrons having a lower average energy than said first neutron generator.

32. The method of claim 31, wherein said second generator is at least one selected from the group consisting of a D—D generator and an isotopic generator.

33. The method of claim 32, further comprising the step of moderating neutrons emitted by said second generator prior to irradiating the bulk material.

34. The method of claim 20, wherein said bulk material is at least one sow.

35. A method of moisture detection, comprising the steps of:
providing at least one neutron generator for neutron bombardment of a material, and at least one gamma ray detector for detection of gamma rays emitted said material responsive to said neutron bombardment, and structure for analyzing gamma ray data communicably connected to said gamma ray detector, said structure for analyzing gamma ray data adapted to determine the presence of water if present in said material;
irradiating said material with said emitted neutrons, and
determining the presence and concentration of water in said material and associated locations in said material having said water, said locations represented in at least 2-dimensions.

36. The method of claim 35, wherein said locations are represented in 3-dimensions.

37. A method for identifying discrete locations of contaminants in materials for recycling, comprising the steps of:
providing a bulk material for recycling;
providing at least one neutron generator for neutron bombardment of said bulk material, and at least one gamma ray detector for detection of gamma rays emitted by contaminants within said bulk material, and structure for analyzing gamma ray data communicably connected to said gamma ray detector, said structure for analyzing gamma ray data adapted to determine the presence of at least one contaminant in said bulk material;
irradiating a first portion of said bulk material with said emitted neutrons;
determining the presence and concentration of said contaminants in said first portion from gamma rays emitted from said first portion;
moving said neutron generator to permit irradiation of an other portion of said bulk material, said other portion different from said first portion;
irradiating said other portion of said bulk material with said emitted neutrons, and
determining the presence and concentration of said contaminants in said other portion from gamma rays emitted from said other portion.

38. The method of claim 37, wherein said first portion comprises substantially an entire portion of said bulk material, and said other portion is a portion less than said entire bulk material.

39. The method of claim 38, further comprising the step of scanning at least one of said neutron generators across a surface of said bulk material, wherein a plurality of said other portions are tested.

* * * * *